US008026377B2

(12) United States Patent
Kaul et al.

(10) Patent No.: US 8,026,377 B2
(45) Date of Patent: *Sep. 27, 2011

(54) PROCESS FOR (3R, 5R)-7-[2-(4-FLUOROPHENYL)-5-ISOPROPYL-3-PHENYL-4-[(4-HYDROXY METHYL PHENYL AMINO) CARBONYL]-PYRROL-1-YL]-3,5-DIHYDROXY-HEPTANOIC ACID HEMI CALCIUM SALT

(75) Inventors: Vijay Kaul, New Delhi (IN); Gyan Chand Yadav, Ghaziabad (IN)

(73) Assignee: Ranbaxy Laboratories, Limited, New Delhi (IN)

( * ) Notice: Subject to any disclaimer, the term of this patent is extended or adjusted under 35 U.S.C. 154(b) by 395 days.

This patent is subject to a terminal disclaimer.

(21) Appl. No.: 12/092,620

(22) PCT Filed: Nov. 7, 2006

(86) PCT No.: PCT/IB2006/054154
§ 371 (c)(1),
(2), (4) Date: Jun. 13, 2008

(87) PCT Pub. No.: WO2007/054896
PCT Pub. Date: May 18, 2007

(65) Prior Publication Data
US 2008/0287690 A1  Nov. 20, 2008

(30) Foreign Application Priority Data

Nov. 8, 2005  (IN) ........................... 2964/DEL/2005
Nov. 8, 2005  (IN) ........................... 2967/DEL/2005
Nov. 14, 2005 (IN) ........................... 3033/DEL/2005

(51) Int. Cl.
*C07D 207/34* (2006.01)
(52) U.S. Cl. ...................................... 548/537
(58) Field of Classification Search ................... 548/537
See application file for complete search history.

(56) References Cited

U.S. PATENT DOCUMENTS

| 3,262,977 A | 7/1966 | Harsanyi et al. |
| 3,341,584 A | 9/1967 | Larsen |
| 3,454,635 A | 7/1969 | Weber |
| 3,471,515 A | 10/1969 | Troxler |
| 3,483,221 A | 12/1969 | Wilhelm |
| 3,527,761 A | 9/1970 | Archibald |
| 3,562,257 A | 2/1971 | Kugita |
| 3,576,883 A | 4/1971 | Neuworth |
| 3,642,896 A | 2/1972 | Collin |
| 3,644,353 A | 2/1972 | Lunts et al. |
| 3,649,691 A | 3/1972 | Shavel |
| 3,655,663 A | 4/1972 | Wasson |
| 3,663,570 A | 5/1972 | Sato |
| 3,663,706 A | 5/1972 | Hess et al. |
| 3,669,968 A | 6/1972 | Hess |
| 3,674,836 A | 7/1972 | Creger |
| 3,705,233 A | 12/1972 | Lunts et al. |
| 3,716,583 A | 2/1973 | Nakamura et al. |
| 3,723,446 A | 3/1973 | Scherm et al. |
| 3,773,939 A | 11/1973 | Janssen |
| 3,781,328 A | 12/1973 | Witte |
| 3,850,941 A | 11/1974 | Irikura |
| 3,857,891 A | 12/1974 | Holmes et al. |
| 3,857,952 A | 12/1974 | Wooldridge et al. |
| 3,868,460 A | 2/1975 | Koppe et al. |
| 3,879,554 A | 4/1975 | Temperilli |
| 3,910,924 A | 10/1975 | Tamura et al. |
| 3,912,743 A | 10/1975 | Christensen et al. |
| 3,932,400 A | 1/1976 | Hibino et al. |
| 3,932,645 A | 1/1976 | Meyer et al. |
| 3,934,032 A | 1/1976 | Barrett et al. |
| 3,937,838 A | 2/1976 | Wetterlin et al. |
| 3,948,943 A | 4/1976 | Eberhardt et al. |
| 3,962,238 A | 6/1976 | Mauvernay et al. |
| 3,982,021 A | 9/1976 | Hauck et al. |
| 3,984,413 A | 10/1976 | Metz et al. |
| 3,994,974 A | 11/1976 | Murakami et al. |
| 3,997,666 A | 12/1976 | Witte et al. |
| 3,998,790 A | 12/1976 | Brandstrom et al. |
| 4,011,258 A | 3/1977 | Wetterlin et al. |
| 4,012,444 A | 3/1977 | Lunts et al. |
| 4,032,648 A | 6/1977 | Malen et al. |
| 4,034,009 A | 7/1977 | Zolss et al. |
| 4,051,143 A | 9/1977 | Scherm et al. |
| 4,056,626 A | 11/1977 | Ito et al. |
| 4,058,552 A | 11/1977 | Mieville |
| 4,062,950 A | 12/1977 | Frommer et al. |

(Continued)

FOREIGN PATENT DOCUMENTS

CN   1436174   8/2003
(Continued)

OTHER PUBLICATIONS

Byrn et al., Chapter 11 Hydrates and Solvates in Solid-State Chemistry of Drugs (2nd Ed.), 1999, 233-247.*
Morissette et al. Adv. Drug Delivery Rev. 2004, 56, 275-300.*
Chapter 10 in Neal G. Anderson, Practical Process Research & Development (2000), pp. 203-221.*
Baumann et al., "The Convergent Synthesis of CI-981, an Optically Active, Highly Potent, Tissue Selective Inhibitor of HMG-COA Reductase", Tetrahedron Letters, Elsevier, vol. 33, No. 17, Apr. 21, 1992, pp. 2283-2284.
International Search Report for International (PCT) Patent Application No. PCT/IB2006/054154, mailed Apr. 3, 2007.
Written Opinion for International (PCT) Patent Application No. PCT/IB2006/054154, mailed Apr. 3, 2007.
Anari et al., "Bridging cheminformatic metabolite prediction and tandem mass spectrometry," DDT, May 2005, vol. 10, pp. 711-717.

(Continued)

*Primary Examiner* — Jason M Nolan
(74) *Attorney, Agent, or Firm* — Sheridan Ross, P.C.

(57) ABSTRACT

The present invention relates to processes for the manufacture of (3R,5R)-7-[2-(4-fluorophenyl)-5-isopropyl-3-phenyl-4-[(4-hydroxy methyl phenyl amino)carbonyl]-pyrrol-1-yl]-3,5-dihydroxy-heptanoic acid hemi calcium salt.

7 Claims, No Drawings

U.S. PATENT DOCUMENTS

| | | | |
|---|---|---|---|
| 4,105,776 A | 8/1978 | Ondetti et al. |
| 4,129,565 A | 12/1978 | Fukushima et al. |
| 4,154,839 A | 5/1979 | Wehinger et al. |
| 4,182,767 A | 1/1980 | Murai et al. |
| 4,188,390 A | 2/1980 | Campbell |
| 4,217,305 A | 8/1980 | Imai et al. |
| 4,248,883 A | 2/1981 | Sawayama et al. |
| 4,252,721 A | 2/1981 | Silvestrini et al. |
| 4,252,825 A | 2/1981 | Demarne |
| 4,252,984 A | 2/1981 | Manoury et al. |
| 4,258,062 A | 3/1981 | Jonas et al. |
| 4,260,622 A | 4/1981 | Junge et al. |
| 4,264,611 A | 4/1981 | Berntsson et al. |
| 4,310,549 A | 1/1982 | Hajos et al. |
| 4,314,081 A | 2/1982 | Molloy et al. |
| 4,337,201 A | 6/1982 | Petrillo, Jr. |
| 4,344,949 A | 8/1982 | Hoefle et al. |
| 4,410,520 A | 10/1983 | Watthey |
| 4,425,355 A | 1/1984 | Hoefle et al. |
| 4,434,176 A | 2/1984 | Troxler et al. |
| 4,444,779 A | 4/1984 | Kawamatsu et al. |
| 4,448,964 A | 5/1984 | Muto et al. |
| 4,466,972 A | 8/1984 | Neumann |
| 4,470,972 A | 9/1984 | Gold et al. |
| 4,472,380 A | 9/1984 | Harris et al. |
| 4,503,067 A | 3/1985 | Wiedemann et al. |
| 4,508,729 A | 4/1985 | Vincent et al. |
| 4,522,828 A | 6/1985 | Jeffery et al. |
| 4,572,909 A | 2/1986 | Campbell et al. |
| 4,587,258 A | 5/1986 | Gold et al. |
| 4,598,089 A | 7/1986 | Hadvary et al. |
| 4,663,325 A | 5/1987 | Ohtaka et al. |
| 4,672,068 A | 6/1987 | Kutsuma et al. |
| 4,681,893 A | 7/1987 | Roth |
| 4,687,777 A | 8/1987 | Meguro et al. |
| 4,699,905 A | 10/1987 | Yanagisawa et al. |
| 4,701,559 A | 10/1987 | Horii et al. |
| 4,705,797 A | 11/1987 | Nardi et al. |
| 4,731,478 A | 3/1988 | Niigata et al. |
| 4,734,280 A | 3/1988 | Braquet |
| 4,801,599 A | 1/1989 | Semeraro et al. |
| 4,822,818 A | 4/1989 | Oka et al. |
| 4,873,259 A | 10/1989 | Summers, Jr. et al. |
| 4,879,303 A | 11/1989 | Davison et al. |
| 4,994,461 A | 2/1991 | Ulrich |
| 5,002,953 A | 3/1991 | Hindley |
| 5,049,559 A | 9/1991 | Braquet et al. |
| 5,128,355 A | 7/1992 | Carini et al. |
| 5,155,103 A | 10/1992 | Weber et al. |
| 5,155,120 A | 10/1992 | Lazar et al. |
| 5,185,351 A | 2/1993 | Finkelstein et al. |
| 5,273,995 A | 12/1993 | Roth |
| 5,274,094 A | 12/1993 | Whittaker et al. |
| 5,344,914 A | 9/1994 | Gibson et al. |
| 5,349,056 A | 9/1994 | Panayotatos |
| 5,356,896 A | 10/1994 | Kabadi et al. |
| 5,385,929 A | 1/1995 | Bjorge et al. |
| 5,399,578 A | 3/1995 | Buhlmayer et al. |
| 5,422,351 A | 6/1995 | Piwinski et al. |
| 5,424,286 A | 6/1995 | Eng |
| 5,466,823 A | 11/1995 | Talley et al. |
| 5,474,995 A | 12/1995 | Ducharme et al. |
| 5,491,172 A | 2/1996 | Lee et al. |
| 5,492,906 A | 2/1996 | Braquet et al. |
| 5,510,332 A | 4/1996 | Kogan et al. |
| 5,541,183 A | 7/1996 | Park et al. |
| 5,552,438 A | 9/1996 | Christensen, IV |
| 5,559,233 A | 9/1996 | Bernhart et al. |
| 5,624,941 A | 4/1997 | Barth et al. |
| 5,633,272 A | 5/1997 | Talley et al. |
| 5,693,675 A | 12/1997 | Mandeville, III et al. |
| 5,712,298 A | 1/1998 | Amschler |
| 5,733,931 A | 3/1998 | Yamada et al. |
| 5,744,501 A | 4/1998 | Norden |
| 5,753,653 A | 5/1998 | Bender et al. |
| 5,767,115 A | 6/1998 | Rosenblum et al. |
| 5,932,598 A | 8/1999 | Talley et al. |
| 5,968,982 A | 10/1999 | Voss et al. |
| 5,985,322 A | 11/1999 | Anderson et al. |
| 5,990,173 A | 11/1999 | Patoiseau et al. |
| 5,994,510 A | 11/1999 | Adair et al. |
| 6,015,557 A | 1/2000 | Tobinick et al. |
| 6,147,090 A | 11/2000 | DeNinno et al. |
| 6,197,786 B1 | 3/2001 | DeNinno et al. |
| 6,268,392 B1 | 7/2001 | Keller et al. |
| 6,329,336 B1 | 12/2001 | Bridon et al. |
| 6,329,344 B1 | 12/2001 | Arora et al. |
| 6,395,751 B1 | 5/2002 | DeNinno et al. |
| 6,420,417 B1 | 7/2002 | Keller et al. |
| 6,426,365 B1 | 7/2002 | Shinkai et al. |
| 6,489,478 B1 | 12/2002 | DeNinno et al. |
| 6,511,985 B1 | 1/2003 | Ippen et al. |
| 6,534,088 B2 | 3/2003 | Guivarc'h et al. |
| 6,569,461 B1 | 5/2003 | Tilyer et al. |
| 6,586,448 B1 | 7/2003 | DeNinno et al. |
| 6,590,085 B1 | 7/2003 | Arora et al. |
| 6,642,268 B2 | 11/2003 | Keller et al. |
| 6,753,346 B2 | 6/2004 | Shinkai et al. |
| 6,787,570 B2 | 9/2004 | Sikorski et al. |
| 6,794,396 B2 | 9/2004 | Lee et al. |
| 6,803,388 B2 | 10/2004 | Sikorski et al. |
| 6,884,226 B2 | 4/2005 | Pereira |
| 6,992,194 B2 | 1/2006 | Lidor-Hadas et al. |
| 7,056,936 B2 | 6/2006 | Kilian et al. |
| 7,361,772 B2 | 4/2008 | Mathew et al. |
| 2002/0052312 A1 | 5/2002 | Reiss et al. |
| 2002/0183378 A1 | 12/2002 | Aronhime et al. |
| 2003/0153617 A1 | 8/2003 | Dalen et al. |
| 2004/0029962 A1 | 2/2004 | Chen et al. |
| 2004/0053842 A1 | 3/2004 | Nguyen et al. |
| 2004/0097555 A1 | 5/2004 | Ohkawa et al. |
| 2004/0102511 A1 | 5/2004 | Sattigeri et al. |
| 2004/0132771 A1 | 7/2004 | Babcock et al. |
| 2005/0032878 A1 | 2/2005 | Deboeck et al. |
| 2005/0063911 A1 | 3/2005 | Nilsson et al. |
| 2005/0187204 A1 | 8/2005 | Kondo et al. |
| 2007/0238716 A1 | 10/2007 | Murthy et al. |
| 2007/0259874 A1 | 11/2007 | Palle et al. |
| 2008/0153896 A1 | 6/2008 | Yadav et al. |
| 2008/0248035 A1 | 10/2008 | Sattigeri et al. |

FOREIGN PATENT DOCUMENTS

| | | |
|---|---|---|
| EP | 0247633 | 12/1987 |
| EP | 0409281 | 1/1991 |
| EP | 0419049 | 3/1991 |
| EP | 0542355 | 5/1993 |
| EP | 0542356 | 5/1993 |
| EP | 0606646 | 7/1994 |
| EP | 0651739 | 5/1995 |
| EP | 0680963 | 11/1995 |
| EP | 0753298 | 1/1997 |
| EP | 0818197 | 1/1998 |
| EP | 0818448 | 1/1998 |
| EP | 0842943 | 5/1998 |
| EP | 0903353 | 3/1999 |
| EP | 0905139 | 3/1999 |
| EP | 0918059 | 5/1999 |
| EP | 1488808 | 12/2004 |
| EP | 1510208 | 3/2005 |
| EP | 1523316 | 4/2005 |
| JP | 2003-104883 | 4/2003 |
| RU | 2279430 | 7/2006 |
| UA | 72290 | 9/2002 |
| WO | WO 95/15973 | 6/1995 |
| WO | WO 95/28926 | 11/1995 |
| WO | WO 96/01644 | 1/1996 |
| WO | WO 96/06108 | 2/1996 |
| WO | WO 96/20216 | 7/1996 |
| WO | WO 96/22966 | 8/1996 |
| WO | WO 96/31206 | 10/1996 |
| WO | WO 96/40641 | 12/1996 |
| WO | WO 96/40781 | 12/1996 |
| WO | WO 97/02289 | 1/1997 |
| WO | WO 97/03094 | 1/1997 |
| WO | WO 97/16184 | 5/1997 |
| WO | WO 97/22619 | 6/1997 |
| WO | WO 98/19998 | 5/1998 |

| | | |
|---|---|---|
| WO | WO 98/27098 | 6/1998 |
| WO | WO 98/47892 | 10/1998 |
| WO | WO 98/53814 | 12/1998 |
| WO | WO 98/53817 | 12/1998 |
| WO | WO 98/53818 | 12/1998 |
| WO | WO 98/54207 | 12/1998 |
| WO | WO 99/11259 | 3/1999 |
| WO | WO 99/20110 | 4/1999 |
| WO | WO 99/23063 | 5/1999 |
| WO | WO 99/24398 | 5/1999 |
| WO | WO 99/35163 | 7/1999 |
| WO | WO 99/36393 | 7/1999 |
| WO | WO 99/37605 | 7/1999 |
| WO | WO 99/37618 | 7/1999 |
| WO | WO 99/43642 | 9/1999 |
| WO | WO 99/47138 | 9/1999 |
| WO | WO 99/47547 | 9/1999 |
| WO | WO 99/54321 | 10/1999 |
| WO | WO 99/58505 | 11/1999 |
| WO | WO 99/58902 | 11/1999 |
| WO | WO 99/61465 | 12/1999 |
| WO | WO 99/67230 | 12/1999 |
| WO | WO 00/00477 | 1/2000 |
| WO | WO 00/01690 | 1/2000 |
| WO | WO 00/05223 | 2/2000 |
| WO | WO 00/05224 | 2/2000 |
| WO | WO 00/15612 | 3/2000 |
| WO | WO 00/18759 | 4/2000 |
| WO | WO 00/18760 | 4/2000 |
| WO | WO 00/35425 | 6/2000 |
| WO | WO 00/43384 | 7/2000 |
| WO | WO 01/13953 | 3/2001 |
| WO | WO 01/32127 | 5/2001 |
| WO | WO 01/37831 | 5/2001 |
| WO | WO 01/42246 | 6/2001 |
| WO | WO 01/53257 | 7/2001 |
| WO | WO 01/93860 | 12/2001 |
| WO | WO 01/96311 | 12/2001 |
| WO | WO 02/13797 | 2/2002 |
| WO | WO 02/43732 | 6/2002 |
| WO | WO 02/051804 | 7/2002 |
| WO | WO 02/096422 | 12/2002 |
| WO | WO 03/007993 | 1/2003 |
| WO | WO 03/013607 | 2/2003 |
| WO | WO 03/013608 | 2/2003 |
| WO | WO 03/066063 | 8/2003 |
| WO | WO 03/077896 | 9/2003 |
| WO | WO 03/080070 | 10/2003 |
| WO | WO 03/088962 | 10/2003 |
| WO | WO 03/094923 | 11/2003 |
| WO | WO 2004/004777 | 1/2004 |
| WO | WO 2004/004778 | 1/2004 |
| WO | WO 2004/014896 | 2/2004 |
| WO | WO 2004/019985 | 3/2004 |
| WO | WO 2004/028456 | 4/2004 |
| WO | WO 2004/039373 | 5/2004 |
| WO | WO 2004/056359 | 7/2004 |
| WO | WO 2004/056395 | 7/2004 |
| WO | WO 2004/062557 | 7/2004 |
| WO | WO 2004/067006 | 8/2004 |
| WO | WO 2004/098583 | 11/2004 |
| WO | WO 2004/106299 | 12/2004 |
| WO | WO 2005/009340 | 2/2005 |
| WO | WO 2005/014539 | 2/2005 |
| WO | WO 2005/018626 | 3/2005 |
| WO | WO 2005/021515 | 3/2005 |
| WO | WO 2005/026163 | 3/2005 |
| WO | WO 2005/034908 | 4/2005 |
| WO | WO 2005/041864 | 5/2005 |
| WO | WO 2005/051931 | 6/2005 |
| WO | WO 2005/056536 | 6/2005 |
| WO | WO 2005/058813 | 6/2005 |
| WO | WO 2005/058898 | 6/2005 |
| WO | WO 2005/100318 | 10/2005 |
| WO | WO 2005/100331 | 10/2005 |
| WO | WO 2006/085212 | 8/2006 |
| WO | WO 2006/117743 | 11/2006 |
| WO | WO 2007/054789 | 5/2007 |
| WO | WO 2007/054790 | 5/2007 |
| WO | WO 2007/054896 | 5/2007 |

OTHER PUBLICATIONS

Fura, A., "Role of pharmacologically active metabolites in drug discovery and development," DDT, Feb. 2006, vol. 11, pp. 133-142.
Giron, "Applications of Thermal Analysis and Coupled Techniques in Pharmaceutical Industry," J. Therm. Anal. Cal., 2002, vol. 68, pp. 335-357.
Giron, "Investigations of Polymorphism and Pseudo-Polymorphism in Pharmaceuticals by Combined Thermoanalytical Techniques," J. Therm. Anal. Cal., 2001, vol. 64, pp. 37-60.
Nedderman, "Metabolites in Safety Testing: Metabolite Identification Strategies in Discovery and Development," Biopharm. Drug Dispos., 2009, vol. 30, pp. 152-162.
Patani et al., "Bioisosterism: A Rational Approach in Drug Design," Chem. Rev., 1996, vol. 96, pp. 3147-3176.
Rautio et al., "Prodrugs: design and clinical applications," Nature Reviews Drug Discovery, 2008, vol. 7, pp. 255-270.
Rodriguez-Spong et al., "General principles of pharmaceutical solid polymorphism: A supramolecular perspective," Advanced Drug Delivery Reviews, 2004, vol. 56, pp. 241-274.
Smith, "Do prodrugs deliver?" Current Opinion in Drug Discovery & Development, 2007, vol. 10, pp. 550-559.
Souliac et al, "Characterization of Delivery Systems, Differential Scanning Calorimetry," pp. 217-218 (in Encyclopedia of Controlled Drug Delivery, 1999, John Wiley & Sons, pp. 212-227).
Testa, "Prodrugs: bridging pharmacodynamic/pharmacokinetic gaps," Current Opinion in Chemical Biology, 2009, vol. 13, pp. 338-344.
Wang et al., "Drug Delivery: Principles and Applications," John Wiley & Sons, Inc. Publication, 2005, Section 8.3, pp. 136-137.
"Prevent" definition from dictionary.com, accessed Nov. 28, 2007.
Carr et al., "Enzymatic Determination of Triglyceride, Free Cholesterol, and Total Cholesterol in Tissue Lipid Extracts", Clin. Biochem., 26:39-42 (1993).
Ruys et al., "The Estimation of Serum Triglycerides by Nephelometry: A Simple Method for the Estimation of Serum Triglycerides Suitable for the Small Laboratory", Med. J. Aust., 22(1):385-387 (1975).
Niculescu-Duvaz D et al., "Self-Immolative Nitrogen Mustard Prodrugs for Suicide Gene Therapy", J. Med. Chem. 41(26):5297-5309 (1998).
Nakanishi, K., "Terpene trilactones from Gingko bioloba: From ancient times to the 21st century", Bioorg. Med. Chem., 13:4987-5000 (2005).
Rinaldi-Carmona et al., "Biochemical and Pharmacological Characterisation of SR141716A, the first potent and selective brain cannabinoid receptor antagonist", Life Sci., 56:1941-1947 (1995).
Rodriguez-Sureda et al., "A Procedure for measuring triacylglyceride and cholesterol content using a small amount of tissue", Anal. Biochem., 343:277-282 (2005).
Karimi et al., "Lithium triflate (LiOTf) catalyzed efficient and chemoselective tetrahydropyranylation of alcohols and phenols under mild and neutral reaction conditions", Tetrahedron Lett., 43(30):5353 (2002).
Wilson et al., "Estimation of VLDL cholesterol in hyperlipidemia", Clin. Chim. Acta., Oct. 15; 1513:285-291 (1985).
Zhang et al., "Niacin mediates lipolysis in adipose tissue through its G-protein coupled receptor HM74A", Biochem and Biophys. Res. Commun., 334:729-732 (2005).
U.S. Appl. No. 12/092,813, filed May 6, 2008, Sattigeri et al.
U.S. Appl. No. 10/558,859, filed Nov. 30, 2005, Salman et al.
Allain et al., Clin. Chem., 20:470 (1974).
Antibacterial & Antifungal Drug Discovery & Development Summit, Strategic Research Institute, Jun. 28-29, 2001, Amsterdam, The Netherlands.
Bedford et al., "Nonquaternary Cholinesterase Reactivators. 3. 3(5)-Substituted 1,2,4-Oxadiazol-5(3)-aldoximes and 1,2,4-Oxidiazole-5(3)-thiocarbohydroximates as Reactivators of Organophosphonate-Inhibited Eel and Human Acetylcholinesterase in Vitro", Journal of Medicinal Chemistry, 29(11):2174-2183 (1986).

Cui et al., J. Biol. Chem., 278:10214-10220 (2003).

Dolinsky et al., Biochem. J., 378:967-974 (2004).

Frederikson et al., J. Lipid Res., 45:592-601 (2004).

Friedewald et al., Clin. Chem., 18:6, pp. 499-502 (1972).

Frings et al., Clin. Chem., 18(7), pp. 673-674 (1972).

Fujino et al., "Metabolic properties of the acid and lactone froms of HMG-CoA reductasse inhibitors", Xenobiotica, Nov./Dec. 2004, vol. 34, No. 11/12, pp. 961-971.

Harwood et al., J. Lipid Res., 34:377-395 (1993).

Heller et al., "Solubilization and Partial Purification of Hepatic 3-Hydroxy-3Methylglutaryl Coenzyme A Reductase," Biochemical and Biophysical Research Communications, 50(3): 859-865 (1973).

Kubo and Strott, "Differential Activity of 3-Hydroxy-3-Methylglutaryl Coenzyme A Reductase in Zones of the Adrenal Cortex," Endocrinology, 120(1):214-221 (1987).

Lorenzen et al., Mol. Pharmacol., 59:349-357 (2001).

Meyer et al., "Annulation of a,b-Unsaturated Ketones by a Micael Addition-Cyclization Sequence. A Versatile Syntesis of Alicyclic Six-Membered Rings", Journal of Organice Chemistry, 50(4):438-447 (1985).

Renodon-Corniere et al., "N-Aryl N'Hydroxyguanidines, A New Class of NO-Donors after Selective Oxidation by Nitric Oxide Synthases: Structure-Activity Relationship," Journal of Medicinal Chemistry, 45(4):944-954 (2002).

Rifai et al., Clin. Chem., 32(6):957-961 (1986).

Sampson et al., Clin. Chem., 47(3):532-539 (2001).

Shefer et al., J. Lipid Res., 22:532-536 (1981).

Sun et al., "A general Sythesis of dioxolenone prodrug moieties", Tetrahedron Letters, 43:1161-1164 (2002).

U.S. Appl. No. 60/498,947, filed Aug. 29, 2003, entitled "Isoxazoline derivatives as inhibitors or phophodiesterase type-IV".

International Preliminary Report on Patentability for International (PCT) Patent Application No. PCT/IB2006/054154, mailed May 22, 2008.

Athyros et al., "Atorvastatin and Micronized Fenofibrate Alone and in Combination in Type 2 Diabetes with Combined Hyperlipidemia," Diabetes Care, 2002, vol. 25, pp. 1198-1202.

Bravo, et al., "Prevalence of Potentially Severe Drug-Drug Interactions in Ambulatory Patients with Dyslipidaemia Receiving HMG-CoA Reductase Inhibitor Therapy," Drug Safety 2005: 28(3):263-275.

Wilke, et al., "Relative impact of CYP3A genotype and concomitant medication on the severity of atorvastatin-induced muscle damage," Pharmacogenetics and Genomics 2005, 15(6):415-421.

Translation of First Office Action for Chinese Patent Application No. 200680041619.0, dispatched Jun. 28, 2010.

Brittain, ed., Polymorphism in Pharmaceutical Solids, vol. 95, 1999, Taylor & Francis, pp. 1-219.

Byrn et al., "Pharmaceutical Solids: A Strategic Approach to Regulatory Considerations," Pharmaceutical Research, 1995, vol. 12, No. 7, pp. 945-954.

Official Action (with English translation) for China Patent Application No. 200680041619.0, dated Mar. 2, 2011, 11 pages.

Examiner's Report for Australia Patent Application No. 2006313430, dated May 5, 2011, 3 pages.

Official Action for European Patent Application No. 06821365.1, dated Jun. 15, 2011, 4 pages.

* cited by examiner

PROCESS FOR (3R, 5R)-7-[2-(4-FLUOROPHENYL)-5-ISOPROPYL-3-PHENYL-4-[(4-HYDROXY METHYL PHENYL AMINO) CARBONYL]-PYRROL-1-YL]-3,5-DIHYDROXY-HEPTANOIC ACID HEMI CALCIUM SALT

CROSS REFERENCE TO RELATED APPLICATIONS

This application is a national stage application under 35 U.S.C. 371 of PCT Application No. PCT/IB2006/054154 having an international filing date of Nov. 7, 2006, which designated the United States, which PCT application claimed the benefit of Indian Application Serial No. 2964/DEL/2005, filed Nov. 8, 2005; Indian Application Serial No. 2967/DEL/2005, filed Nov. 8, 2005 and Indian Application Serial No. 3033/DEL/2005, filed Nov. 14, 2005. The entire disclosure of each of these priority documents is incorporated herein by reference.

FIELD OF THE INVENTION

The present invention relates to processes for the manufacture of (3R,5R)-7-[2-(4-fluorophenyl)-5-isopropyl-3-phenyl-4-[(4-hydroxy methyl phenyl amino)carbonyl]-pyrrol-1-yl]-3,5-dihydroxy-heptanoic acid hemi calcium salt.

BACKGROUND OF THE INVENTION

Cardiovascular disease and its associated maladies, dysfunctions and complications are a principal cause of disability and the chief cause of death. One specific factor significantly contributing to this pathophysiologic process is atherosclerosis, which has been generally recognized as a leading health care problem both with respect to mortality and health care costs. Atherosclerosis is characterized by the deposition of fatty substances, primarily cholesterol, resulting in plaque formation on the inner surface of the arterial wall and degenerative change to the arteries.

It is now well established that cardiovascular disorders including myocardial infarction, coronary heart disease, hypertension and hypotension, cerebrovascular disorders including stroke, cerebral thrombosis and memory loss due to stroke; peripheral vascular disease and intestinal infarction are caused by blockage of arteries and arterioles by atherosclerotic plaque. Atherosclerotic plaque formation is multifactorial in its production. Hypercholesterolemia, especially elevated levels of low-density lipoprotein cholesterol (LDL), is an important risk factor for atherosclerosis and arteriosclerosis and associated diseases.

The HMG-CoA reductase inhibitors (statins) have been used in reducing blood levels of LDL cholesterol. Cholesterol is produced via the mevalonic acid pathway. Reducing the formation of mevalonic acid, a precursor to cholesterol, leads to a corresponding decrease in hepatic cholesterol biosynthesis with a reduction in the cellular pool of cholesterol. PCT Publication No. WO 2004/106299 discloses (3R,5R)-7-[2-(4-fluorophenyl)-5-isopropyl-3-phenyl-4-[(4-hydroxy methyl phenyl amino)carbonyl]-pyrrol-1-yl]-3,5-dihydroxy-heptanoic acid hemi calcium salt, having the Formula I,

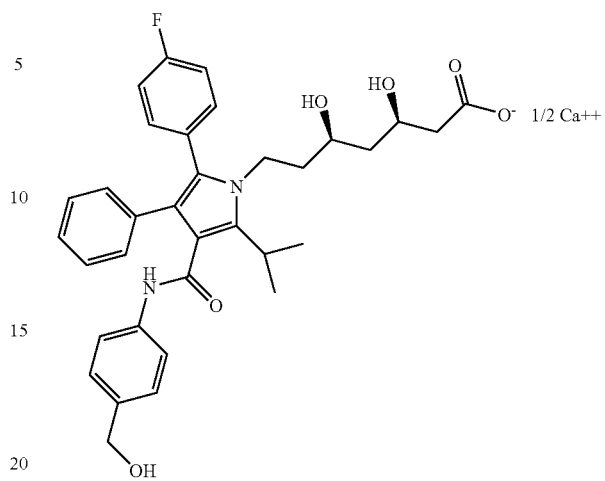

Formula I as an effective HMG-CoA (3-hydroxy-3-methylglutaryl-coenzyme A) reductase inhibitor and thus is useful as hypolipidemic and hypocholesterolemic agent.

A procedure for the synthesis of (3R,5R)-7-[2-(4-fluorophenyl)-5-isopropyl-3-phenyl-4-[(4-hydroxy methyl phenyl amino)carbonyl]-pyrrol-1-yl]-3,5-dihydroxy-heptanoic acid hemi calcium salt is disclosed in WO 2004/106299. The aforementioned synthetic route involves isolation and purification of intermediates at each step of the process by column chromatography. However, the total overall yield is low, and the high cost of production render the process not amenable to large scale manufacture.

SUMMARY OF THE INVENTION

In one aspect, herein are provided improved processes for the manufacture of compound of Formula I, described above, at a commercial scale.

In another aspect, herein are provided improved processes which avoid the use of column chromatography as a purification method, and are cost effective and easily amenable to large-scale production.

In yet another aspect, herein are provided processes of making high purity compound of Formula I with increased overall yield by employing reaction conditions that include various solvents and solvent combinations, temperature conditions, time period and work-up procedures at each stage of the process. Also, in still another aspect, herein is provided isolation of intermediates of high purity with superior yields without resorting to purification by column chromatography at any stage of the process.

In still another aspect, herein are provided one-pot processes for the conversion of a particular dihydroxy compound to the desired calcium salt of Formula I in the final step, thus making the processes more economical.

As discussed, herein are provided processes for the preparation of a compound of Formula I.

Formula I
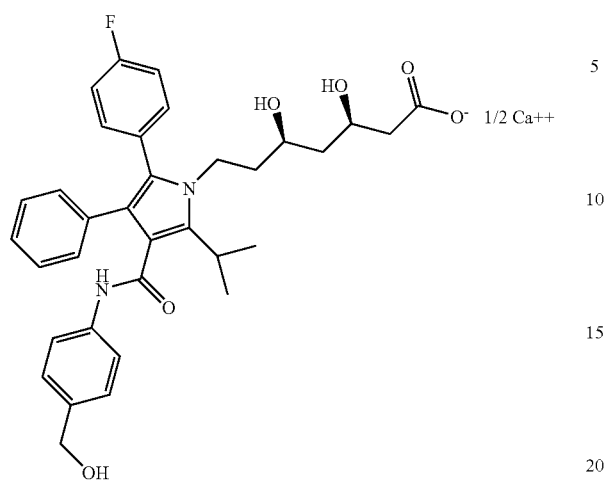
DETAILED DESCRIPTION OF THE INVENTION
The compound of Formula I, (3R,5R)-7-[2-(4-fluorophenyl)-5-isopropyl-3-phenyl-4-[(4-hydroxymethylphenyl amino)carbonyl]-pyrrol-1-yl]-3,5-dihydroxy-heptanoic acid hemi calcium salt can be prepared by, for example, the following reaction sequence as depicted in Scheme I.
Scheme I
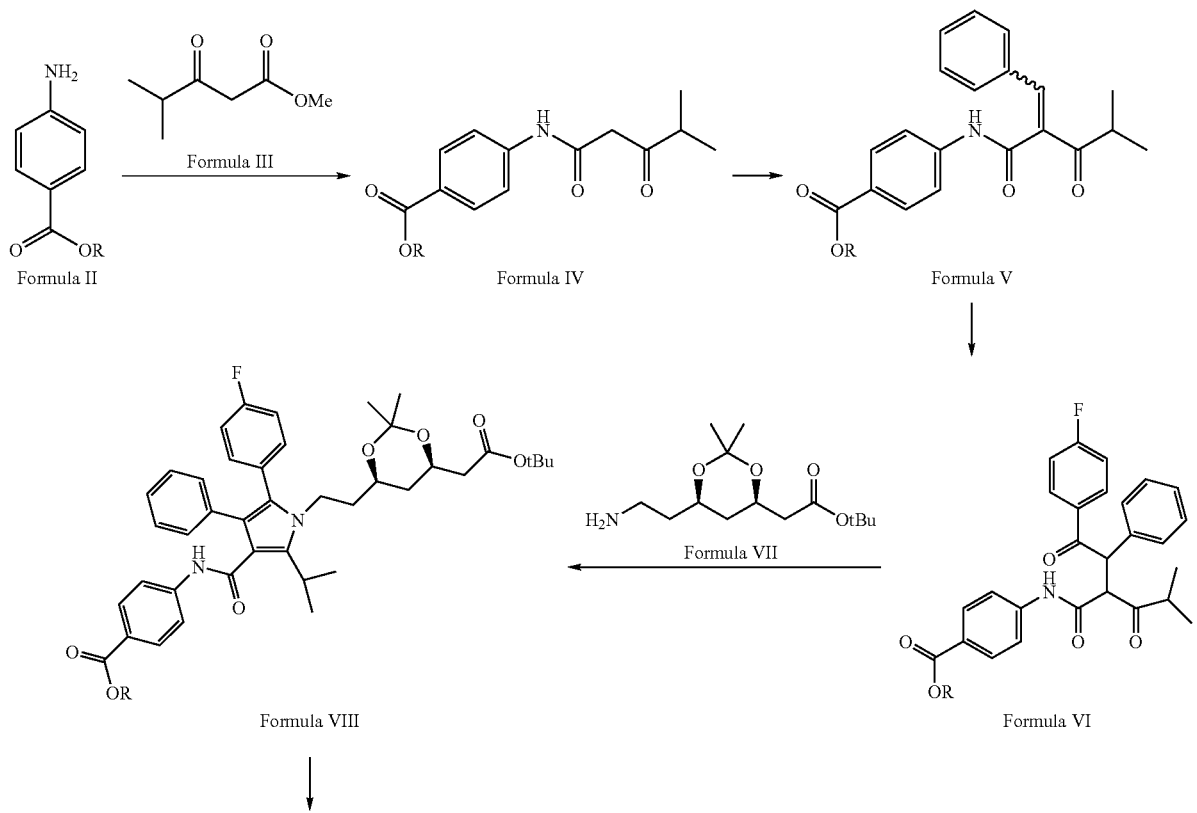

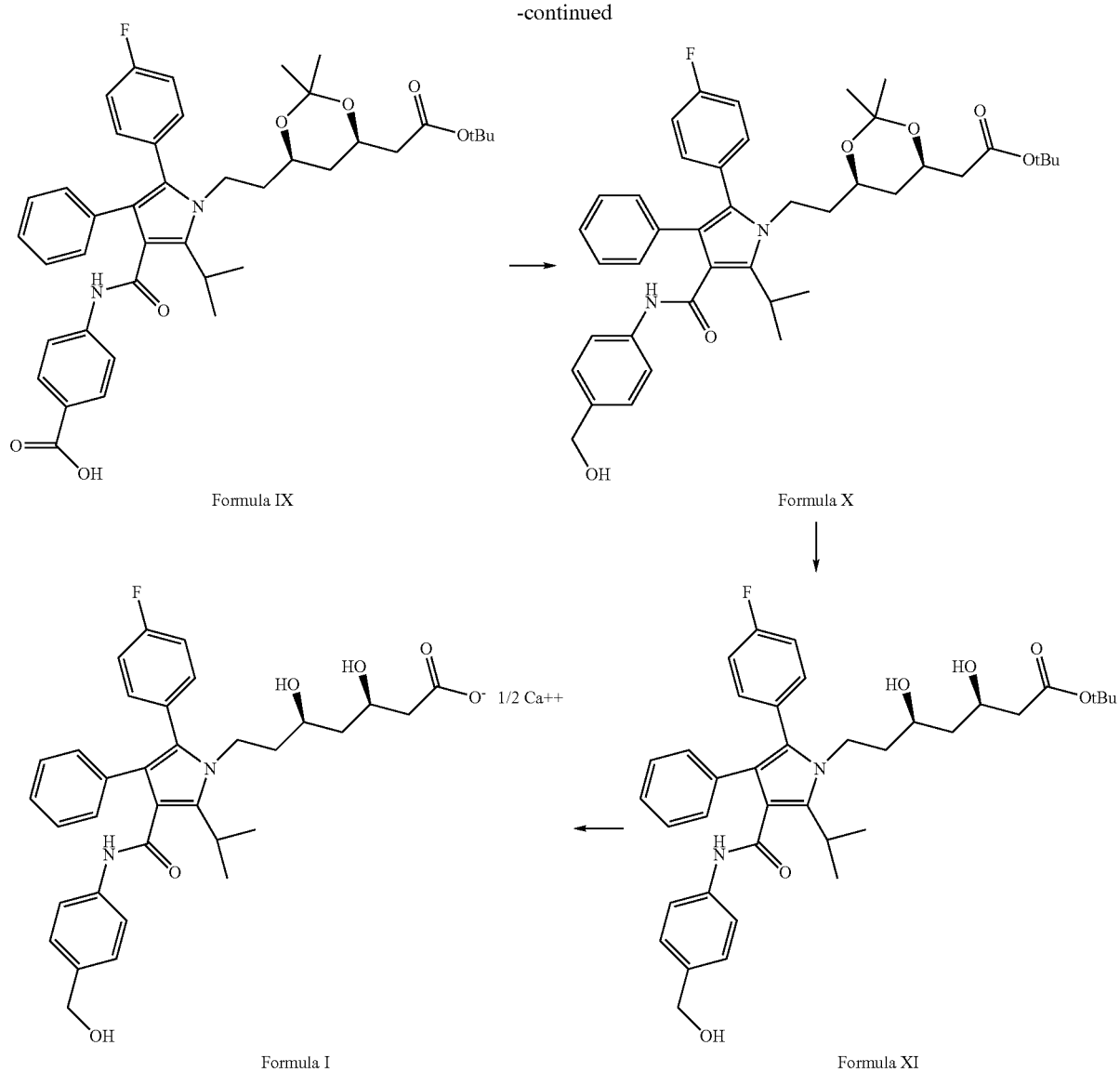

Formula IX

Formula X

Formula I

Formula XI

Thus, the amine of Formula II when reacted with methyl-4-methyl-3-oxopentanoate in refluxing hydrocarbon solvent can result in a β-ketoamide of Formula IV (wherein R is aryl, alkyl or arylalkyl). The compound of Formula IV on reaction with benzaldehyde can afford a compound of Formula V, which is a mixture of E & Z isomers. The compound of Formula V on subjecting to acylion condensation with 4-fluorobenzaldehyde can afford a 1,4 diketo compound of Formula VI. The compound of Formula VI on condensation with chiral amine of Formula VII can result in a compound of Formula VIII, which on subsequent deprotection can give a compound of Formula IX. Selective reduction of carboxyl group in compound of Formula IX can afford a compound of Formula X. Acid catalyzed cleavage of the ketal group in compound of Formula X can result in a dihydroxy compound of Formula XI which can be converted into calcium salt of the desired Formula I in two ways:
   i) by directly converting the compound of Formula XI into its hemi calcium salt of Formula I under phase transfer catalysis using Ca(OH)$_2$, or
   ii) by converting the compound of Formula XI to its sodium salt, generated in situ, using sodium hydroxide and subsequent displacement of sodium with Ca using calcium acetate or calcium chloride to generate the hemi calcium salt of Formula I.

The reaction of an amine of Formula II with 4-methyl-3-oxopentanoate can be carried out in one or more solvents, for example, hydrocarbon solvents (e.g., hexane, heptane, xylene or toluene, in presence of an organic base, for example, triethylamine, pyridine or 1,2-ethylenediamine in a catalytic amount.

The reaction of a compound of Formula IV with benzaldehyde can be carried out in one or more solvents, for example, hexane, heptane or toluene, in presence of an organic base, for example, piperidine, pyridine or β-alanine, and an organic acid, for example, glacial acetic acid or benzoic acid.

The reaction of a compound of Formula V with 4-fluorobenzaldehyde can be carried out in presence of a catalyst (e.g., sodium cyanide, 3-ethyl-5-(2-hydroxy-ethyl)-4-methyl thiazolium bromide or 3-benzyl-5-(2-hydroxyethyl)-4-methyl thiazolium chloride), in a solvent-free environment, or in a solvent, for example, polar solvent (e.g., methanol, ethanol, propanol or isopropanol), ether solvent (e.g., dioxane, diethyl ether or tetrahydrofuran) or mixtures thereof, or in presence of an organic base (e.g., triethylamine or pyridine). Alternatively, the reaction can be carried out in the presence of excess base, for example, triethylamine which itself acts as a solvent.

The reaction of a compound of Formula VI with a compound of Formula VII can be carried out in one or more solvents, for example, hydrocarbon solvents (e.g., xylene, toluene, hexane or heptane), ether solvents (e.g., tetrahydrofuran or dioxane) or mixtures thereof, in the presence of an organic acid, for example, pivalic acid or p-toluene sulfonic acid.

The deprotection of a compound of Formula VIII can be carried out at temperatures ranging from about 10° C. to reflux temperature, for example, at temperatures ranging from about 40 to about 50° C., in presence of an inorganic base (e.g., sodium hydroxide, potassium hydroxide, lithium hydroxide, calcium hydroxide, sodium carbonate, potassium carbonate, sodium bicarbonate or potassium bicarbonate); in one or more solvents, for example, polar solvents (e.g., methanol, ethanol, acetonitrile, isopropyl alcohol or t-butanol) or ether solvents (e.g., tetrahydrofuran, diethyl ether or dioxane) or mixtures thereof. Alternatively, deprotection can be carried out under phase transfer catalysis using TBAB in aqueous alcoholic solvents, for example, ethanol or methanol at reflux temperatures.

The reduction of a compound of Formula IX can be carried out in presence of a reducing agent (e.g., boron-dimethylsulfide complex or boron-tetrahydrofuran complex); in one or more solvents, for example, hydrocarbon solvents (e.g., hexane, n-heptane or toluene), ether solvents (e.g., tetrahydrofuran, dioxane or diethyl ether) or mixtures thereof.

The cleavage of the ketal group of a compound of Formula X with an acid (e.g., hydrochloric acid) can be carried out at temperatures ranging from about room temperature (about 25° C.) to reflux temperature, preferably at temperatures ranging from about 40 to about 55° C. in one or more solvents, for example, polar solvents (e.g., methanol, ethanol or isopropyl alcohol), ether solvents (e.g., tetrahydrofuran, dioxane or diethyl ether) or combination thereof.

The compound of Formula XI can be converted into its corresponding hemi calcium salt of formula I either:
i) by first converting Formula XI compound into its sodium salt by treatment with NaOH at temperature ranging from about 0 to about 30° C., for example, at temperature ranging from about 0 to about 10° C. and subsequent displacement of sodium with calcium using calcium acetate in the presence of one or more alcoholic solvents, for example, methanol, ethanol, etc. or ether solvents (e.g., tetrahydrofuran, dioxane or diethyl ether) or combinations thereof, or
ii) by subjecting Formula XI compound to phase transfer catalysis using tetrabutylammonium bromide as the catalyst and calcium hydroxide as the base in refluxing aqueous alcoholic solvent, for example, methanol or ethanol.

The process described above may involve one or more of the following embodiments. For example, the reaction of the compound of Formula II can be carried out in toluene. The reaction of the compound of Formula V can be carried out in presence of triethylamine, which itself can act as a solvent. The reaction of the compound of Formula VIII can be carried out in acetonitrile or methanol:tetrahydrofuran (1:3), in presence of sodium hydroxide at temperatures ranging from about 50 to about 55° C. for about 4-5 hours or, for example, at about 30° C. for about 8-10 hours. The reaction of the compound of Formula IX can be carried out at temperatures ranging from about 40 to about 45° C. for about 5 hours. The reaction of the compound of Formula X can be carried out in methanol:tetrahydrofuran:water (1:1:1). The reaction of the compound of Formula XI can be carried out tetrahydrofuran:de-ionized water (1:1) or ethanol:water (4:1), in presence of tetrabutylammonium bromide at a temperature ranging from about 30 to about 50° C. for about 2-8 hours.

The process as enumerated above has an advantage that, none of the steps involve the use of column chromatography as a purification method, thus enables such processes to achieve high yields and makes them amenable to large-scale production.

The compound of Formula IV can be purified by dissolving the crude product of Formula IV in ethyl acetate and washing the ethyl acetate layer successively with an acid then by de-ionized water, the excess acid can be removed by washing the solution successively with sodium bicarbonate solution, de-ionized water, concentrated to obtain a solid, which can be added to hexane and stirred till the product precipitates out, which is filtered and dried.

The compound of Formula V can be purified by washing the crude product of Formula V with hexane to remove the organic impurities followed by drying the product, which can be dissolved in ethyl acetate and partitioned with de-ionized water to remove the inorganic impurities, the organic layer can be separated, dried and dissolved in isopropyl alcohol with heating, which on cooling can give the solid product, filtered and dried in vacuum tray drier at temperatures ranging from about 40 to about 50° C. for about 6 hours.

The compound of Formula VI can be purified by dissolving the crude product of Formula VI and activated charcoal in a solvent system of methanol and water and refluxing the reaction mixture, filtered and the residue so obtained can be washed with solvent methanol:water (9:1), the filtrate can be concentrated to obtain a solid, slurred in hexane, filtered, and concentrated under vacuum.

The compound of Formula VIII can be purified by cooling the reaction mixture to about 0° C. and stirring till the product precipitates, which can be filtered, washed with hexane, and dried.

The compound of Formula IX can be purified by a) cooling the reaction mixture to room temperature and acidifying it, filtering to get the solid and washing it with de-ionized water and acetonitrile, the solid can be further refluxed in denatured spirit, cool till the product precipitates out, filtered, washed with denatured spirit, and dried under vacuum, b) concentrating the reaction mixture and extracting it into a solvent system of ethyl acetate and water, separating the ethyl acetate layer and washing it with brine, the organic layer can be further acidified wherein, the excess acid can be neutralized by a base and washed with de-ionized water, the reaction mixture can be concentrated and the residue can be triturated with hexane to form solid, filtered, and dried under vacuum.

The compound of Formula X can be purified by a) dissolving the crude product in ethyl acetate and washing the layer successively with de-ionized water, sodium bicarbonate and brine, concentrated to obtain a solid, which can be slurred in hexane, filtered and dried under vacuum, b) dissolving the crude product in the solvent system of isopropyl alcohol, de-ionized water and acetic acid, and refluxing it with concurrent addition of calcium hydroxide, the hot solution can be filtered, the filtrate so obtained can be cooled to room temperature till the solid precipitates out, filtered, washed with ice-cold isopropyl alcohol and water, dried in vacuum tray drier at about 60° C. for about 7-8 hours.

The compound of Formula XI can be purified by a) dissolving the crude product in a solvent system of ethyl acetate and toluene (1:2) and washing the layer successively with de-ionized water and brine, the product can be isolated, slurred in hexane at about 40° C. for about 1 hour, cooled, filtered and dried in vacuum tray drier at about 60° C. for about 3 hours, b) dissolving the crude product in (10%) ethyl acetate-hexane solvent system with concurrent heating at temperatures ranging from about 40 to about 50° C. for about 1 hour, cooled to room temperature (about 25° C.) and stirred for about 1 hour or till the product precipitates, the solid so obtained can be filtered, washed with water and hexane and dried in vacuum tray drier.

The compound of Formula I can be purified by a) washing the crude product with ethyl acetate and drying it under vacuum at temperatures ranging from about 60 to about 70° C. for about 10 hours, dissolved in methanol and to it can be added butylated hydroxy anisole, the solution can be filtered to obtain a solid, which can be dried in vacuum tray drier at temperatures ranging from about 40 to about 50° C. to form pure amorphous compound, b) refluxing the crude calcium salt in a solvent system of ethyl acetate and water (1:1) and butylated hydroxy anisole, the hot solution can be filtered, the filtrate can be cooled till the product completely precipitates out, filtered, washed with ethyl acetate and dried under vacuum to form pure amorphous compound, c) filtering the hot reaction mixture, the filtrate so obtained can be cooled and to it can be added de-ionized water, the product precipitates out, filtered, subjected to reflux in ethyl acetate and water mixture (1:1); the reaction mixture can be cooled till the product precipitates out, which can be followed by isolating the product, washing it with ethyl acetate and drying it in vacuum tray drier to form pure amorphous compound.

In the above reaction scheme, where specific reducing agents, solvents, bases, catalysts, acids etc., are mentioned, it is to be understood that other reducing agents, solvents, bases, catalysts, acids etc., known to those skilled in the art may be used. Similarly, the reaction temperature and duration may be adjusted. While the present invention has been described in terms of its specific embodiments, certain modifications and equivalents will be apparent to those skilled in the art and are included within the scope of the present invention.

EXAMPLES

Example 1

Preparation of Methyl 4-[(4-methyl-3-oxopentanoyl)amino]benzoate of Formula IV

To a solution of methyl-4-aminobenzoate (250 g, 1.65 moles) in toluene (2.4 L) was added methyl-4-methyl-3-oxopentanoate (237.7 g, 1.648 moles) and ethylene diamine (1.15 ml, 0.016 moles). The reaction mixture was refluxed for about 20-25 hours. The solvent was removed under reduced pressure to obtain a solid residue. The residue was dissolved in ethyl acetate (2.4 L). The organic phase was washed with an acid (e.g., 20% w/w hydrochloric acid 0.5 L) followed by de-ionized water. It was further washed with a 10% sodium bicarbonate solution, followed by de-ionized water and saturated brine. The solvent was removed under reduced pressure. To this was added hexane while stirring and the solid precipitated out completely. The solid was filtered and washed with hexane. The solid was dried to yield the title product in 99.45% purity.

Yield: 358 g (1.5, w/w); LCMS: m/z (M+1) 265.09; Melting range: 54-56° C.; $^1$H NMR (CDCl$_3$): δ 1.16-1.18 (d, 6H, —CH(CH$_3$)$_2$), 2.75-2.70 (m, 1H, —CH(CH$_3$)$_2$), 3.62 (s, 2H, CH$_2$), 3.89 (s, 3H, OCH$_3$), 7.62-7.65 (d, 2H, ArH), 7.98-8.01 (d, 2H, ArH), 9.51 (bs, NHCO).

Example 2

Preparation of Methyl 4-{[-2-benzylidene-4-methyl-3-oxopentanoyl]amino}benzoate of Formula V To a mixture of compound of Formula IV (400 g, 1.52 moles) and benzaldehyde (177 g, 1.67 moles) in hexane (5.4 L) was added β-alanine (27 g, 0.3 moles) followed by glacial acetic acid (54.6 g, 0.91 moles) while under stirring. The reaction mixture was refluxed for about 24 hours with constant removal of moisture with the help of a Dean-Stark apparatus. At the end of the reaction, solid precipitated. The solid was filtered and washed with hexanes (0.6 L). The solid was dissolved in ethyl acetate (3.6 L) followed by addition of de-ionized water (1.2 L) with stirring. The layers were separated and the organic layer was washed with brine. The solvent was removed under reduced pressure to obtain a solid product, which was dissolved in isopropyl alcohol (0.85 L) on heating. The solution was cooled to room temperature and the solid precipitated. The solid was filtered and successively washed with ice-cold isopropyl alcohol and hexanes. The solid was dried under vacuum (10 mbar) at about 40 to about 50° C. for about 6 hours to obtain the desired product as a mixture of E & Z isomers.

Yield: 338 g (0.84, w/w); LCMS: m/z (M+1) 352.1; Melting range: 154-156° C.; $^1$H NMR (CDCl$_3$):

E isomer: δ 1.21-1.23 (d, 6H, —CH(CH$_3$)$_2$), 3.32-3.39 (m, 1H, —CH(CH$_3$)$_2$), 3.90 (s, 3H, OCH$_3$), 7.33-7.39 (m, 3H, Ar H), 7.53-7.59 (m, 4H, ArH), 7.93 (s, 1H, vinylic H), 8.00-8.02 (d, 2H, ArH). (melting range of analytical sample, 155.0-156.2° C.)

Z isomer: δ 1.03-1.05 (d, 6H, —CH(CH$_3$)$_2$), 2.62-2.65 (m, 1H, —CH(CH$_3$)$_2$), 3.91 (s, 3H, OCH$_3$), 7.30-7.32 (m, 2H, Ar H), 7.42-7.45 (m, 3H, ArH), 7.71-7.73 (d, 2H, ArH), 8.03-8.05 (d, 2H, ArH), 8.21 (s, 1H, vinylic H). (Melting range of analytical sample, 145.6-146.3° C.)

Example 3

Preparation of Methyl 4-({2-[2-(4-fluorophenyl)-2-oxo-1-phenylethyl]-4-methyl-3-oxopentanoyl}amino)benzoate of Formula VI To a mixture of compound of Formula V (100 g, 0.285 moles) in triethylamine (0.2 Lt) was added thiazolium bromide (17.94 g, 0.071 moles) and 4-fluorobenzaldehyde (38.82 g, 0.313 moles). The reaction mixture was subjected to reflux for about 8 hours. At the end of the reaction, as indicated by TLC or reaction monitoring by HPLC, triethylamine was removed under reduced pressure. The solid so obtained was dissolved in ethyl acetate (0.75 L) followed by the addition of de-ionized water (0.25 L). The organic phase was then separated and the aqueous layer was washed with ethyl acetate. The combined organic layer was washed successively with de-ionized water, acid (e.g., 10% hydrochloric acid 0.2 L), base (e.g., 10% sodium bicarbonate) and brine. The solvent was removed under reduced pressure to obtain a solid product. The solid was dissolved in a solvent system of methanol and water (9:1, 0.75 L) on heating with added activated charcoal (7.5 g) and brought to reflux. The hot solution was filtered and the residue was washed with solvent system of methanol and water (9:1). The filtrate was further cooled to about 0 to about 5° C. and the solid that precipitated was filtered. The solid was slurred with hexanes (0.4 L) at about 40° C. for 1 hr and was filtered. The product was dried under vacuum (10 mbar) at about 50° C. for about 10 to about 12 hours to give the product of desired quality.

Yield: 156 g (0.93, w/w); Melting range: 168.5-170° C.; LCMS: m/z (M+1) 476.21 $^1$H NMR (CDCl$_3$): δ 1.15-1.18 (d, 3H, —CH$_3$), 1.22-1.25 (d, 3H, —CH$_3$), 2.96-3.02 (m, 1H, CH(CH$_3$)$_2$), 3.89 (s, 3H, —OCH$_3$), 4.54-4.56 (d, 1H, —CO—CH-Ph), 5.33-5.36 (d, 1H, —CO—CH—CO—), 7.01-7.99 (m, 14H, Ar—H and —NH).

Example 4

Preparation of Methyl 4-({[1-{2-[(4R,6R)-6-(2-tert-butoxy-2-oxoethyl)-2,2-dimethyl-1,3-dioxan-4-yl]ethyl}-5-(4-fluorophenyl)-2-isopropyl-4-phenyl-1H-pyrrol-3-yl]carbonyl}amino)benzoate of Formula VIII Pivalic acid (44.2 g, 0.433 moles) was added to a mixture of a compound of Formula VI (200 g, 0.421 moles) and [6-(2-Amino-ethyl)-2,2-dimethyl-[1,3-d]oxan-4-yl]-acetic acid t-butyl ester of Formula VII (137.9 g, 0.505 moles) in solvent system of heptane, toluene and tetrahydrofuran in the ratio of 4:1:1 (2.52 L). The reaction mixture was refluxed for about 28 to about 35 hours. The reaction mixture was cooled to about 0° C. and stirred till the product precipitates. The precipitated product was filtered and washed with hexanes (1 L). The solid was dried under vacuum (10 mbar) at about 50° C. to obtain the desired product.

Yield: 210 g (1.05, w/w); LCMS: m/z (M+1) 713.2; Melting range: 158.8-159.5° C.; $^1$H NMR (CDCl$_3$): δ 1.03-1.06 (m, 1H, >NCH$_2$CH$_2$—), 1.30-1.36 (2×s, 6H, >C(CH$_3$)$_2$ & m, 1H, >NCH$_2$CH$_2$— merged together), 1.43 (s, 9H, —C(CH$_3$)$_3$), 1.52-1.54 (d, 6H, —CH(CH$_3$)$_2$), 1.66 (m, 2H, C-5 —CH$_2$—), 2.2-2.4 (m, 2H, —CH$_2$COO$^t$Bu), 3.6 (m, 1H, —CH(CH$_3$)$_2$), 3.7 (m, 1H, C-4 >CHO—), 3.85 (s, 3H, —OCH$_3$), 3.85 (m, 1H, C-6 >CHO—), 4.1 (m, 2H, >NCH$_2$—), 6.97-7.85 (m, 14H, Ar—H and —NH).

Example 5

Preparation of 4-({[1-{2-[(4R,6R)-6-(2-tert-butoxy-2-oxoethyl)-2,2-dimethyl-1,3-dioxan-4-yl]ethyl}-5-(4-fluorophenyl)-2-isopropyl-4-phenyl-1H-pyrrol-3-yl]carbonyl}amino)benzoic acid of Formula IX Sodium hydroxide (2.5 molar equiv., 1 N aq. soln.) was added to a solution of compound of Formula VIII (425 g, 0.596 moles) in acetonitrile (4.25 L) and the reaction mixture was stirred at about 50-55° C. for about 4-5 hours. The reaction mixture was cooled to about 25° C. and the pH adjusted to 5.5-6 with 20% acetic acid solution when the product precipitated out. The solid was then filtered and washed with de-ionized water and acetonitrile. The crude product obtained was refluxed in denatured spirit (7.2 L) for about 1 hour. The reaction mixture was cooled to about 25° C. and stirred for about 5 hours till the solid precipitated completely. The solid was filtered and washed with denatured spirit (0.42 L). The solid was further dried under vacuum (10 mbar) at about 50° C. for about 6 hours to obtain the desired product.

Yield: 324.95 g (0.76, w/w); LCMS: m/z (M+1) 699.3; Melting range: 239.9-241.7° C.; $^1$H NMR (CDCl$_3$): δ 1.03-1.06 (m, 1H, >NCH$_2$CH$_2$—), 1.30-1.36 (2×s, 6H, >C(CH$_3$)$_2$ & m, 1H, >NCH$_2$CH$_2$— merged together), 1.43 (s, 9H, —C(CH$_3$)$_3$), 1.52-1.54 (d, 6H, —CH(CH$_3$)$_2$), 1.64-1.68 (m, 2H, C-5—CH$_2$—), 2.2-2.4 (m, 2H, —CH$_2$COO$^t$Bu), 3.6 (m, 1H, —CH(CH$_3$)$_2$), 3.7 (m, 1H, C-4 >CHO—), 3.8 (m, 1H, C-6 >CHO—), 4.15-4.17 (m, 2H, >NCH$_2$—), 6.97-7.92 (m, 14H, ArH and —NH).

Alternatively, sodium hydroxide (2.5 eq., 1 N aq. soln.) was added to a solution of compound of Formula VIII (100 g, 0.14 moles) in a mixture of tetrahydrofuran and methanol (1.0 L, 3:1) and the reaction mixture was stirred at room temperature (30° C.) for about 8-10 hours. The volatilities were distilled at reduced pressure and ethyl acetate and water (1:1) charged under stirring at room temperature. The organic phase was separated and washed with saturated brine; any insoluble material that precipitated was filtered. The pH of the organic phase was adjusted to 5.5-6 with 20% acetic acid solution and subsequently washed with de-ionized water and bicarbonate solution. The organic volatilities were removed under reduced pressure and the residue was triturated with hexanes to give the solid, which was filtered and washed with hexanes. The solid was further dried under vacuum (10 mbar) at about 50° C. for about 6 hours to obtain the desired product.

Yield: 60 g (0.6, w/w).

Example 6

Preparation of tert-butyl((4R,6R)-6-{2-[2-(4-fluorophenyl)-4-({[4-(hydroxymethyl)phenyl]amino}carbonyl)-5-isopropyl-3-phenyl-1H-pyrrol-1-yl]ethyl}-2,2-dimethyl-1,3-dioxan-4-yl)acetate of Formula X A solution of a compound of Formula IX (100 g, 0.14 moles) in tetrahydrofuran (0.7 L) was heated to about 40-45° C. To it was added boron-dimethyl sulfide complex (BMS complex 2.3 eq., 2M soln. in tetrahydrofuran). The reaction mixture was stirred at this same temperature for about 5 hours. The reaction mixture was cooled to about 20-25° C. and to it was added methanol to destroy excess BMS complex. The organic volatilities were removed under vacuum and the residue so obtained was dissolved in ethyl acetate. The organic phase was successively washed with de-ionized water, sodium bicarbonate and brine. On distilling the solvent under reduced pressure (10 mbar) at 50° C. the desired product obtained was a solid. The solid reaction mass was slurred in hexanes and filtered. The product so obtained was dried under vacuum (10 mbar) at about 60° C. for about 7-8 hours and used for the next step.

Yield: 95 g, (0.95, w/w); LCMS: m/z (M+1) 685.3; Melting range: 193.8-194.6° C.; $^1$H NMR (CDCl$_3$): δ 1.03-1.06 (m, 1H, >NCH$_2$CH$_2$—), 1.30-1.36 (2×s, 6H, >C(CH$_3$)$_2$ & m, 1H, >NCH$_2$CH$_2$— merged together), 1.43 (s, 9H, —C(CH$_3$)$_3$), 1.52-1.54 (d, 6H, —CH(CH$_3$)$_2$), 1.66-1.67 (m, 2H, C-5 —CH$_2$—), 2.2-2.4 (m, 2H, —CH$_2$COO$^t$Bu), 3.58 (m, 1H, —CH(CH$_3$)$_2$), 3.68 (m, 1H, C-6 >CHO—), 3.82 (m, 1H, C-4 >CHO—), 4.07-4.17 (m, 2H, >NCH$_2$—), 4.57 (s, 2H, —PhCH$_2$OH), 6.87-7.21 (m, 14H, ArH and —NH).

Alternatively, the reaction mixture after quenching with methanol to destroy the excess BMS complex is subjected to distillation under reduced pressure to reduce the volatiles to a minimum and allowed to attain ambient temperature. Acetic acid was added to the reaction mixture along with isopropyl alcohol and de-ionized water. The reaction mixture was heated to reflux and calcium hydroxide charged. The reaction mixture was filtered hot and the filtrate on cooling to 20-25° C. results in the precipitation of the solid product, which was filtered and washed with a mixture of chilled isopropyl alcohol and water. The product so obtained was dried under vacuum (10 mbar) at 60° C. for 7-8 hours and the desired product, so obtained was used for the next step.

Example 7

Preparation of (3R,5R)-7-[2-(4-fluorophenyl)-4-({[4-(hydroxymethyl)phenyl]amino}carbonyl)-5-isopropyl-3-phenyl-1H-pyrrol-1-yl]-3,5-dihydroxyheptanoic acid t-butyl ester of Formula XI Hydrochloric acid (1 N, aq soln.) was added to a solution of a compound of Formula X (25 g, 0.036 moles) in a solvent system of methanol and tetrahydrofuran (1:1), 0.125 L at room temperature. The reaction mixture was stirred for about 5 hours or till the completion of the reaction. The reaction mixture was quenched with sodium bicarbonate (1.53 g, 0.018 moles) and subjected to removal of the organic volatilities under reduced pressure. The residue so obtained was taken up in ethyl acetate and toluene (1:2, 0.5 L). The organic phase was washed successively with de-ionized water and brine. Removal of the solvent under vacuum resulted in a solid product. The solid obtained was slurried in hexane at about 40° C. for about 1 hour, followed by cooling to ~25° C. and filtration. The solid obtained was dried under vacuum (20 mm) at about 60° C. for about 3 hours.

Yield: 22 g, (0.88, w/w); LCMS: m/z (M+1) 645.2; Melting range: 144.6-146.1° C.; $^1$H NMR (CDCl$_3$): δ 1.20-1.24 (m, 1H, >NCH$_2$CH$_2$—), 1.40-1.45 (s, 9H, —C(CH$_3$)$_3$ & m, 1H, >NCH$_2$CH$_2$-merged together), 1.52-1.54 (d, 6H, —CH(CH$_3$)$_2$), 1.62 (m, 2H, C-4 CH$_2$(—CHOH)$_2$), 2.3-2.32 (d, 2H, —CH$_2$COO$^t$Bu), 3.56-3.59 (m, 1H, —CH(CH$_3$)$_2$), 3.72 (bs, 2H, 2×OH), 3.78 (m, 1H, C-5 >CHOH), 3.93 (m, 1H, C-3 >CHOH), 4.07-4.14 (m, 2H, >NCH$_2$—), 4.57 (s, 2H, -PhCH$_2$OH), 6.87-7.19 (m, 14H, ArH and —NH).

Alternatively, the compound of formula X (200 g, 0.29 moles) on being subjected to acid hydrolysis in a mixture of tetrahydrofuran:methanol:water (1:1:1, 3 Lt) at about 50° C. in presence of 1 N HCl (0.5, molar equiv.) for about 1-2 hours afforded the desired compound in solution. The reaction mixture was quenched with sodium bicarbonate (15.96 g, 0.19 moles) and the organic volatiles were distilled leaving behind 50% of the total reaction volume. To the reaction mixture was added 10% ethyl acetate in hexanes (2 L) and subjected to a temperature of about 40-50° C. for about 1 hour. The reaction mixture was then cooled to ~25° C. and stirred at this temperature for about 1 hour for complete precipitation. The product so obtained was filtered and washed with water (0.2 L) and hexanes (0.4 L). The solid obtained was dried under vacuum (20 mm) at about 60° C. for about 3 hours. Yield: 0.87 (w/w).

Example 8

Preparation of (3R,5R)-7-[2-(4-fluorophenyl)-4-({[4-(hydroxymethyl) phenyl]amino}carbonyl)-5-isopropyl-3-phenyl-1H-pyrrol-1-yl]-3,5-dihydroxyheptanoic acid hemi calcium salt of Formula I A solution of a compound of Formula XI (60 g, 0.093 moles) in methanol and tetrahydrofuran (1:1, 0.3 L) was stirred at room temperature. The reaction mixture was cooled to 0° C. A solution of sodium hydroxide (1 N aq. soln., 1.2 eq.) was added to the reaction mixture and the temperature was not allowed to exceed 10° C. during addition. The reaction mixture was stirred for about 3 hours at about 5-10° C. The solvent was then removed under reduced pressure. The solid product obtained was dissolved in ethyl acetate (0.3 L); to it was added de-ionized water (0.6 L). The aqueous layer containing the desired product was separated and washed with ethyl acetate. To this aqueous layer was added calcium acetate solution (0.66 L, 0.6 eq.) and stirred till product of Formula I precipitated. The product was filtered and washed with ethyl acetate. The product was dried under vacuum (10 mm) at 60-70° C. for about 10 hours. The product obtained above (50 g, yield 0.833, w/w) was dissolved in methanol (0.245 L) and butylated hydroxy anisole (BHA, 0.05 mol %) was added. The solution so obtained was filtered and evaporated to dryness under vacuum (10 mm) at 40-50° C. to get the desired amorphous form of the compound of Formula I (44 g).

Over all yield: 44 g, (0.73, w/w); LCMS: m/z (M+1) 589.1; $^1$H NMR (CD$_3$OD): δ 1.36-1.39 (m, 1H, C-6 >NCH$_2$CH$_2$), 1.46-1.47 (d, 6H, CH(CH$_3$)$_2$), 1.51-1.53 (m, 1H, C-6 > NCH$_2$CH$_2$ merged with CH(CH$_3$)$_2$), 1.67-1.68 (m, 2H, C-4 C H$_2$(—CHOH)$_2$) 2.22-2.32 (m, 2H, C-2 —CH$_2$COO$^-$), 3.33-3.37 (m, 1H, CH(CH$_3$)$_2$), 3.64-3.65 (m, 1H, C-5 >CHOH), 3.89 (m, 1H, C-3 >CHOH), 3.99-4.06 (m, 2H, C-7 >NC H$_2$—), 4.51 (s, 2H, -PhCH$_2$OH), 7.02-7.12 (m, 7H, ArH), 7.20-7.24 (m, 4H, ArH), 7.27-7.29 (m, 2H, ArH).

Alternatively, the compound of Formula XI (80 g, 0.124 moles) in tetrahydrofuran and deionized water (1:1, 0.8 L) was stirred at room temperature in the presence of sodium hydroxide (1 N aq sol, 1.2 eq.) for about 2-3 hours at about 30° C. The solvent tetrahydrofuran was then removed under reduced pressure and the residue taken up in ethyl acetate water mixture. The aqueous layer containing the desired product was separated and washed with ethyl acetate. To this aqueous layer was added calcium acetate (0.6 eq.) under stirring. The desired product precipitated. To the precipitated product in aqueous solution was added ethyl acetate such that the ratio of ethyl acetate and water is 1:1 and butylated hydroxyl anisole (0.05 mol %) and the reaction mixture was refluxed to dissolve the solids. The hot solution was filtered and allowed to cool to room temperature (25-30° C.) under stirring when the desired Ca-salt of compound of Formula I precipitated. The product was filtered and washed with ethyl acetate. The product was dried under vacuum (10 mm) at 55-65° C. for 10-12 hours, (yield, 60 g, 0.75 w/w). The desired compound of Formula I, was obtained above, and was treated further to produce one single morph consistently, i.e., the amorphous form of compound of Formula I. Thus, to a solution of the compound of Formula I (25 g) in methanol (500 ml) was added butylated hydroxyl anisole (0.05 mol %), filtered and subjected to spray drying technique to give the desired amorphous form (20.5 g).

Yield: 0.82 w/w; Overall yield: 0.61

Alternatively, a mixture of compound of Formula XI (80 gms, 0.124 moles), calcium hydroxide (13.8 g, 0.186 moles) and tetrabutylammonium bromide (2 g, 5 mol %) in ethanol: water mixture (4:1, 0.8 L) was heated to about 50° C. for about 5-8 hours under stirring. Reaction mixture shows consumption of the starting material as indicated by TLC or by HPLC. The reaction mixture was filtered hot (~50° C.). The filtrate was cooled to room temperature (~25° C.) and charged to deionized water (2.4 L) under stirring. The precipitated product was filtered and washed with water (0.16 L) and sucked dry. The wet cake was refluxed in ethyl acetate:water mixture (1:1, 1.6 L) till the complete dissolution of solids. The reaction mixture was cooled to 25° C. under stirring for about 2 hours to afford the compound of Formula I of desired quality. The solid was filtered and washed with ethyl acetate (0.32 L), sucked dry and further dried under the above conditions, yield, 50.5 g (0.63, w/w). Further treatment of the product as described above affords the amorphous compound of Formula I.

We claim:

1. A process of making 3R,5R)-7-[2-(4-fluorophenyl)-5-isopropyl-3-phenyl-4-[(4-hydroxy methyl phenyl amino)carbonyl]-pyrrol-1-yl]-3,5-dihydroxy-heptanoic acid hemi calcium salt of Formula I,

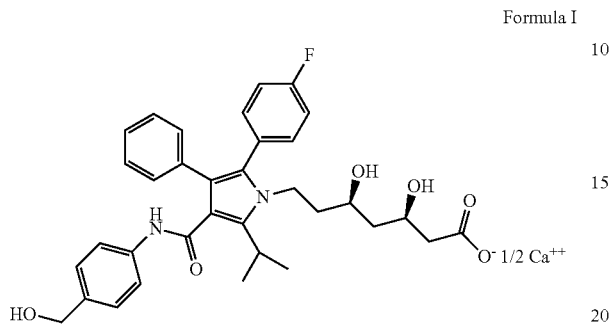

Formula I the method comprising: (a) reacting a compound of Formula II with a compound of Formula III,

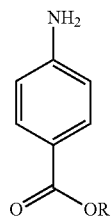

Formula II

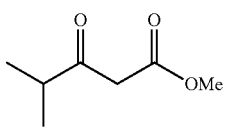

Formula III to form a compound of Formula of IV (wherein R is alkyl, aryl or arylalkyl);

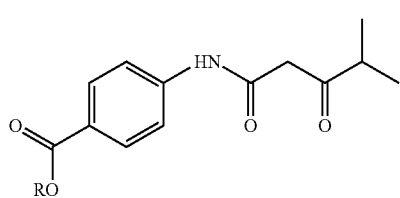

Formula IV (b) reacting the compound of Formula IV with benzaldehyde to form a compound of Formula V;

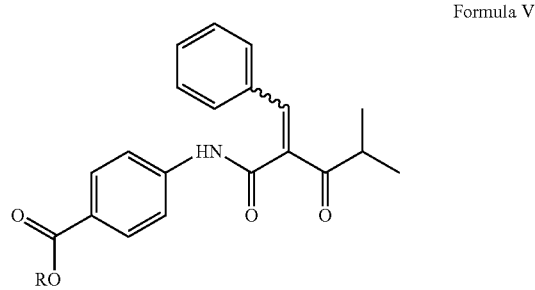

Formula V (c) reacting the compound of Formula V with 4-fluorobenzaldehyde to form a compound of Formula VI;

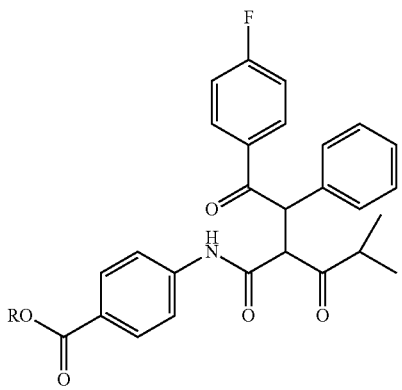

Formula VI (d) reacting the compound of Formula VI with a compound of Formula VII,

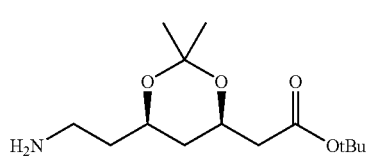

Formula VII to form the compound of Formula VIII;

Formula VIII

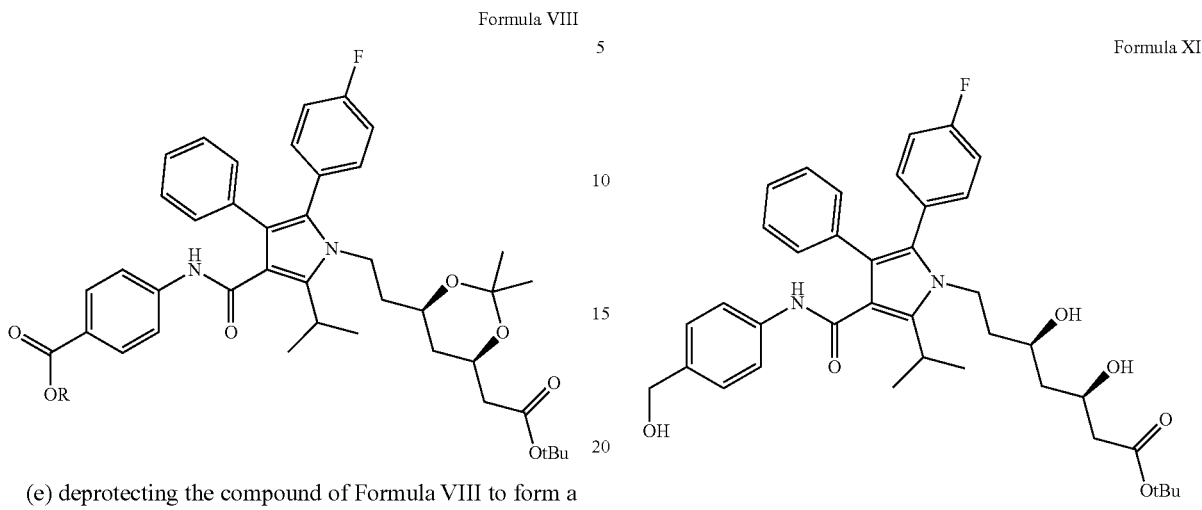

(e) deprotecting the compound of Formula VIII to form a compound of Formula IX;

Formula IX

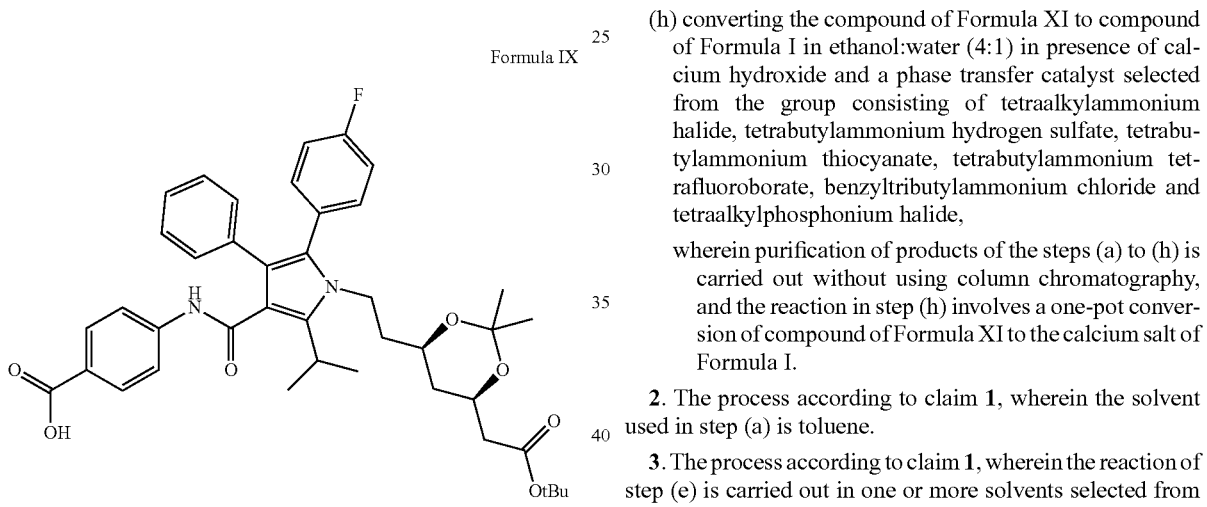

(f) reducing the compound of Formula IX in the presence of a reducing agent and a hydrocarbon solvent to form a compound of Formula X;

Formula X

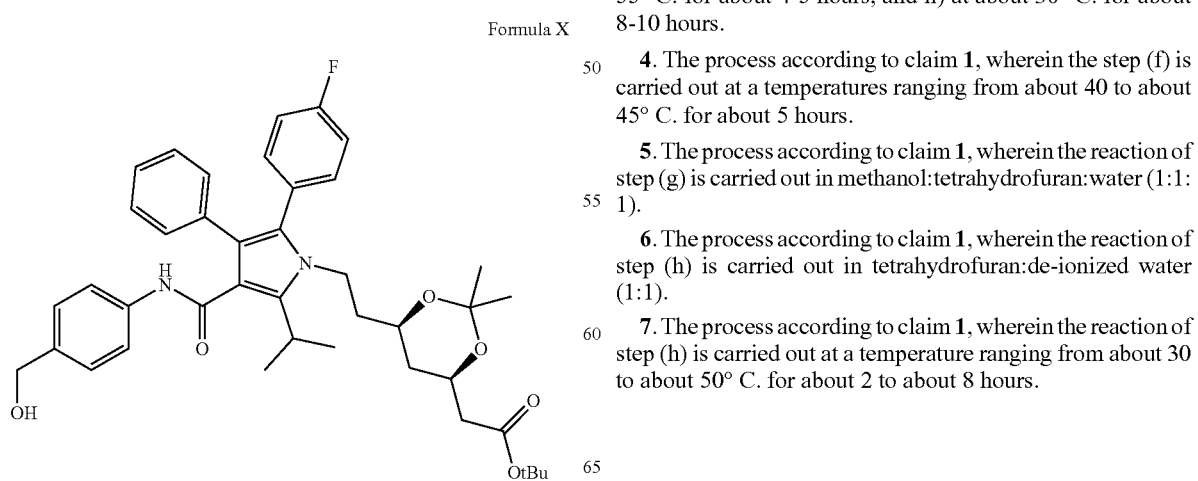

(g) deprotecting the compound of Formula X to form a compound of Formula XI; and Formula XI

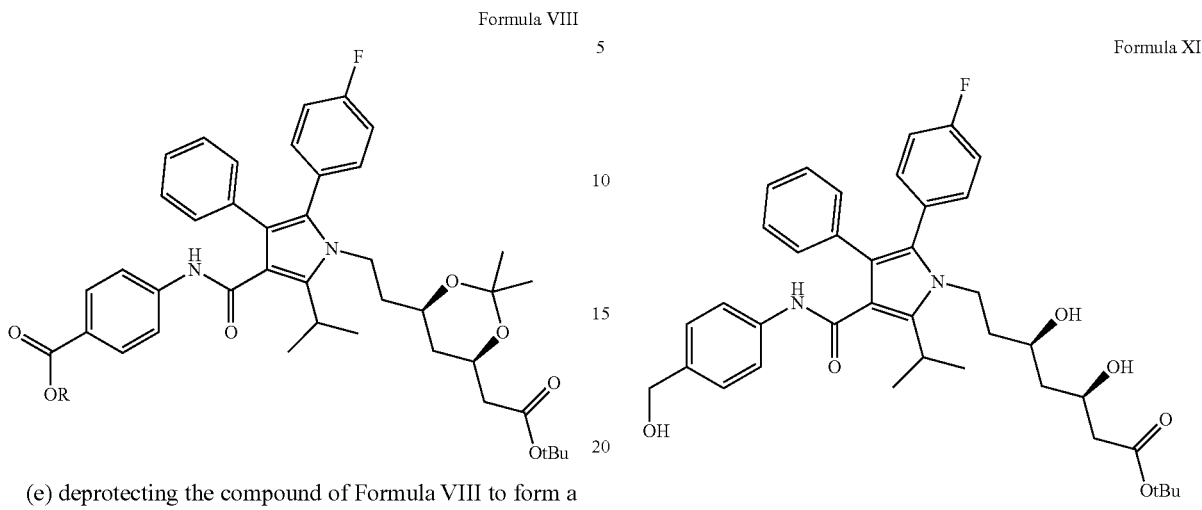

(h) converting the compound of Formula XI to compound of Formula I in ethanol:water (4:1) in presence of calcium hydroxide and a phase transfer catalyst selected from the group consisting of tetraalkylammonium halide, tetrabutylammonium hydrogen sulfate, tetrabutylammonium thiocyanate, tetrabutylammonium tetrafluoroborate, benzyltributylammonium chloride and tetraalkylphosphonium halide, wherein purification of products of the steps (a) to (h) is carried out without using column chromatography, and the reaction in step (h) involves a one-pot conversion of compound of Formula XI to the calcium salt of Formula I.

2. The process according to claim 1, wherein the solvent used in step (a) is toluene.

3. The process according to claim 1, wherein the reaction of step (e) is carried out in one or more solvents selected from acetonitrile, propionitrile, dimethylsulfoxide, dimethylformamide and dimethoxyethane or methanol:tetrahydrofuran (1:3), in the presence of sodium hydroxide, under conditions selected from i) temperatures ranging from about 50 to about 55° C. for about 4-5 hours, and ii) at about 30° C. for about 8-10 hours.

4. The process according to claim 1, wherein the step (f) is carried out at a temperatures ranging from about 40 to about 45° C. for about 5 hours.

5. The process according to claim 1, wherein the reaction of step (g) is carried out in methanol:tetrahydrofuran:water (1:1:1).

6. The process according to claim 1, wherein the reaction of step (h) is carried out in tetrahydrofuran:de-ionized water (1:1).

7. The process according to claim 1, wherein the reaction of step (h) is carried out at a temperature ranging from about 30 to about 50° C. for about 2 to about 8 hours.

* * * * *

UNITED STATES PATENT AND TRADEMARK OFFICE
CERTIFICATE OF CORRECTION

PATENT NO. : 8,026,377 B2  Page 1 of 1
APPLICATION NO. : 12/092620
DATED : September 27, 2011
INVENTOR(S) : Vijay Kaul et al.

It is certified that error appears in the above-identified patent and that said Letters Patent is hereby corrected as shown below:

Please add the following to the list of References cited:

--U.S. Patent No. 5,344,915 to Lemaire et al. (issued on September 6, 1994).--

Signed and Sealed this
Twenty-fifth Day of September, 2012

David J. Kappos
*Director of the United States Patent and Trademark Office*